United States Patent [19]
Brehm et al.

[11] Patent Number: 5,816,800
[45] Date of Patent: Oct. 6, 1998

[54] PALATAL ARCH EXPANDER ASSEMBLY AND METHOD OF ADJUSTING

[75] Inventors: Lindsay W. Brehm, Encinitas; Stephen M. Huff, San Diego; Robert J. Senini, La Costa, all of Calif.

[73] Assignee: Ortho Organizers, Inc., San Marcos, Calif.

[21] Appl. No.: 548,450

[22] Filed: Oct. 26, 1995

[51] Int. Cl.[6] .................................................. A61C 3/00
[52] U.S. Cl. .................................................. 433/7; 433/20
[58] Field of Search .................................. 433/7, 17, 20, 433/21

[56] References Cited

U.S. PATENT DOCUMENTS

| | | | |
|---|---|---|---|
| 1,938,428 | 12/1933 | Johnson | 433/20 |
| 3,162,948 | 12/1964 | Gerber | 433/7 |
| 4,412,819 | 11/1983 | Cannon | 433/20 |
| 4,479,779 | 10/1984 | Wool | 433/20 |
| 4,571,179 | 2/1986 | Balenseifen | 433/20 |
| 4,592,725 | 6/1986 | Goshgarian | 433/7 |
| 4,669,980 | 6/1987 | Degnan | 433/8 |
| 4,815,968 | 3/1989 | Keller | 433/7 |
| 4,818,226 | 4/1989 | Berendt et al. | 433/20 |
| 4,854,864 | 8/1989 | Cleary | 433/7 |
| 4,897,035 | 1/1990 | Green | 433/17 |
| 4,900,251 | 2/1990 | Andreasen | 433/20 |
| 4,976,614 | 12/1990 | Tepper | 433/18 |
| 5,007,828 | 4/1991 | Rosenberg | 433/7 |
| 5,167,499 | 12/1992 | Arndt et al. | 433/7 |
| 5,312,247 | 5/1994 | Sachdeva et al. | 433/7 |
| 5,399,087 | 3/1995 | Arndt | 433/7 |

FOREIGN PATENT DOCUMENTS

| | | | |
|---|---|---|---|
| WO 93/15684 | 8/1993 | WIPO | 433/7 |

OTHER PUBLICATIONS

Hicks, E. Preston, D.D.S., M.S.D., Slow Maxillary Expansion: A Clinical Study of the Skeletal Versus Dental Response to Low–Magnitude Force, *American Journal of Orthodontics*, vol. 73, No. 2, Feb. 1978.

Haas, A. J., D.D.S., M.S., *Long–Term Posttreatment Evaluation of Rapid Palatal Expansion*, Oct. 1979.

Bell, Ronald A., D.D.S, M.D., A Review of Maxillary Expansion in Relation to Rate of Expansion and Patient's Age, *American Journal of Orthodontics*, Jan. 1981.

Muguerza, Oscar E., D.D.S., M.S.D. and Shapiro, Peter A. D.D.S., M.S.D., Palatal Mucoperiostomy: An Attempt ot Reduce Relapse After Slow Maxillary Expansion, *American Journal of Orthodontics*, vol. 78, No. 5, Jan. 1981.

*Primary Examiner*—John J. Wilson
*Attorney, Agent, or Firm*—Fulwider Patton Lee & Utecht, LLP

[57] ABSTRACT

A palatal arch expander assembly provides low, constant expansion forces to the palatal arch and provides individual corrective forces to either the first or second molars. A shape memory or superelastic archwire can be cooled below its transition temperature so that it is easily bendable for insertion into the mouth. After insertion, the archwire warms to a temperature above its transition temperature and provides low, continual expansion forces throughout the treatment period without requiring further adjustment. A pair of adjustment wires are bendable and provide individual corrective forces to either the first or second molars. The adjustment wires can be readjusted at any point during the treatment period. The archwire can be formed from a nickel-titanium alloy wire or superelastic material and the adjustment wires can be formed from nicoloy, stainless steel, or similar metal wire.

16 Claims, 5 Drawing Sheets

FIG. 12B          FIG. 12B

PALATAL ARCH EXPANDER ASSEMBLY AND METHOD OF ADJUSTING

FIELD OF THE INVENTION

The present invention relates generally to orthodontic appliances to move teeth. More specifically, a palatal arch expander assembly is provided to expand the palatal arch and provide corrective forces to the molars.

BACKGROUND OF THE INVENTION

The field of orthodontics is directed primarily to movement of teeth for various reasons, including correcting for malocclusions, expansion of the palatal arch, and moving the teeth en mass. Current orthodontic practice includes use of brackets that are bonded to the buccal surface of the teeth and an archwire attached to the brackets to reposition teeth. There are numerous prior art brackets and archwires available to accomplish the objective, some of which may include so called shape memory or superelastic alloy archwires or the more common stainless steel archwire. The shape memory archwires generally provide low but constant corrective forces throughout the treatment period without removing the wire to add different bending forces. The shape memory wires attempt to return to their original configuration and in so doing, provide the desired corrective forces. On the other hand, stainless steel archwires must be continually readjusted during the treatment period since they lose their tension once the teeth have been moved a prescribed amount. The stainless steel wires provide high corrective forces immediately after adjustment and these forces diminish as the teeth move toward the prescribed position. The stainless steel wires can cause discomfort to the patient immediately after adjustment because the corrective forces are highest at this point.

It is sometimes necessary to provide corrective forces to the palatal arch, generally to expand the arch to add space and to align the molars and the premolars. Prior art devices include use of an archwire attached to the lingual surface of the molars and then providing expansion forces to move the teeth. The purpose in expanding the arch generally is to provide space for the molars or the premolars or to provide space between the teeth when crowding occurs. Some prior art devices include a stainless steel archwire used in conjunction with spreader bars or jackscrew devices which can be adjusted to provide expansion forces and create the necessary spacing between the teeth. These prior art devices typically require numerous visits to the orthodontist so that the device can be readjusted throughout the treatment period and after each visit the patient may experience discomfort due to the large corrective forces resulting from the adjustment.

Other prior art devices include use of a shape memory archwire to expand the arch and provide the desired spacing between the teeth. The benefit of using a shape memory archwire is that it provides low, constant forces and it does not require as many visits to the orthodontist for readjustment. One problem that arises when using a shape memory archwire is that it is difficult to work with in terms of attaching it to the molars. It generally cannot be bent at severe angles (i.e., 180°) and it cannot be heated above certain temperatures, otherwise it will lose its shape memory characteristics.

Other disadvantages of the prior art palatal expansion archwires made from shape memory metals include the inability to readjust the forces distributed to the molars during the treatment period. Once a shape memory archwire is inserted, it will continuously provide constant corrective forces as the archwire attempts to return to its original shape. Unfortunately, the shape of the archwire may not always be the desired shape and there is almost always a need to correct the alignment of the first or second molars by tipping (angulation), rotating, or torquing them. In fact, it may be necessary to correct the alignment of one molar for rotation, and the opposed molar for tipping. The prior art stainless steel and shape memory archwires cannot achieve the most desired result of expanding the palatal arch with low, continuous forces and provide a means of aligning the molars as needed, independent of the forces on each molar and independent of the forces created by the archwire. The present invention satisfies these needs and provides a novel solution to the problems faced by the prior art devices.

SUMMARY OF THE INVENTION

The present invention solves the problems encountered by the prior art devices by allowing the orthodontist to expand the palatal arch using low, continual expansion forces and to align the molars independent of each other and independent of the archwire expanding the arch. The present invention provides an apparatus and method of treatment that is novel and accomplishes what the prior art devices cannot. It is noted that the reference to "molars" is intended to mean either the first molars or the second molars. Thus, for example, when it is said that sheaths are attached to the molars, it is intended that the sheaths are attached to either opposed first molars or opposed second molars, but not both sets of first and second molars.

The present invention provides a palatal arch expander assembly which is inserted into the mouth of a patient and is easily removed when adjustments are required or when the treatment period is complete. The assembly includes an archwire having shape memory or superelastic properties to expand the palatal arch. It also includes a pair of adjustment wires attached to the molars so that each molar can be individually aligned without affecting the opposing molar.

More particularly, the palatal arch expander assembly has an archwire made from an alloy of nickel-titanium (NiTi) which will expand the palatal arch with low, continuous forces. The assembly also includes a pair of adjustment wires attached to the distal ends of the archwire. The adjustment wires can be formed from nicoloy, stainless steel, or a similar material. Each of the adjustment wires has a bend formed in its distal end which can be adjusted to impart corrective forces to the individual molars.

The archwire ends and the distal end of each of the adjustment wires are attached by inserting the ends into a crimp tube and crimping them until they are securely attached. At least a portion of the adjustment wires are inserted into a pair of stems having somewhat of a bayonet configuration. The stems are adapted to insert into sheaths which are mounted on the lingual surface of the molars. Each of the adjustment wires has a bend, which can be approximately 180°, and which is positioned between the crimp tube and the stem. With the bend so positioned, the adjustment wires can be easily adjusted by adjusting the amount of angulation in the bend and by twisting the bend outwardly toward the buccal. By adjusting the bend angulation corrective forces are imparted directly to the molars. The bend angles can impart rotational, angulation, and torquing forces in the molars.

A novel method of insertion and adjustment is provided by the present invention. The palatal arch expander assembly is cooled prior to insertion into the patient's mouth, allowing the NiTi wire to twist and deform so that it can be easily positioned in the mouth. The stems are then aligned with and inserted into the sheaths so that the assembly is removeably attached to the molars. After insertion, the NiTi archwire warms from body heat and it transforms from its martensitic state to its austenitic state where it will attempt to return to its original shape. In its austenitic state, the NiTi archwire is somewhat stiff and inflexible and it provides low, continual forces to expand the palatal arch. Once inserted, the bends in the adjustment wires can be readjusted to rotate, torque or angulate the molars.

The palatal arch expander assembly is easily removed by pulling the stems out of the sheaths and removing the assembly from the patient's mouth. If desired, the bends can be readjusted while the assembly is out of the patient's mouth and then reinserted to continue the treatment process.

These and other features and advantages of the present invention will become apparent to persons of ordinary skill in the art upon reading the detailed description of the invention in connection with the drawings.

BRIEF DESCRIPTION OF THE DRAWINGS

FIG. 12A is a side view of the palatal arch expander assembly depicting the various adjustments available to the bends in the adjustment wires to cause angulation (tipping) in the molars.

DETAILED DESCRIPTION OF THE PREFERRED EMBODIMENT

As used herein, references to "molars" is intend to mean either the first molars or the second molars.

Figure 1:
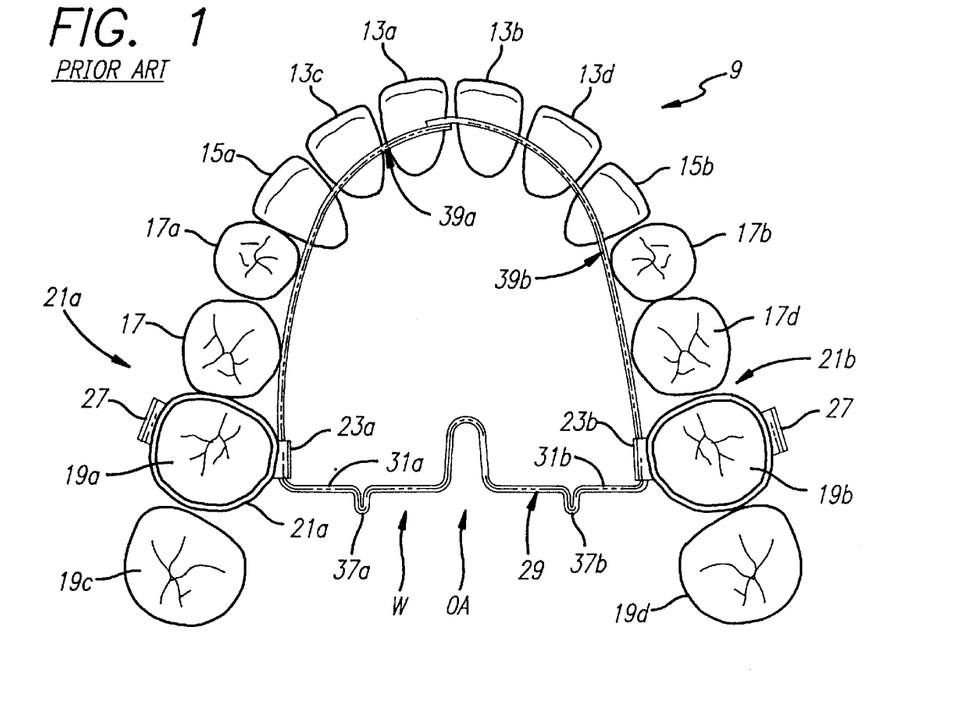
FIG. 1 depicts a prior art palatal arch expander where the archwire is formed from stainless steel.
Figure 2:
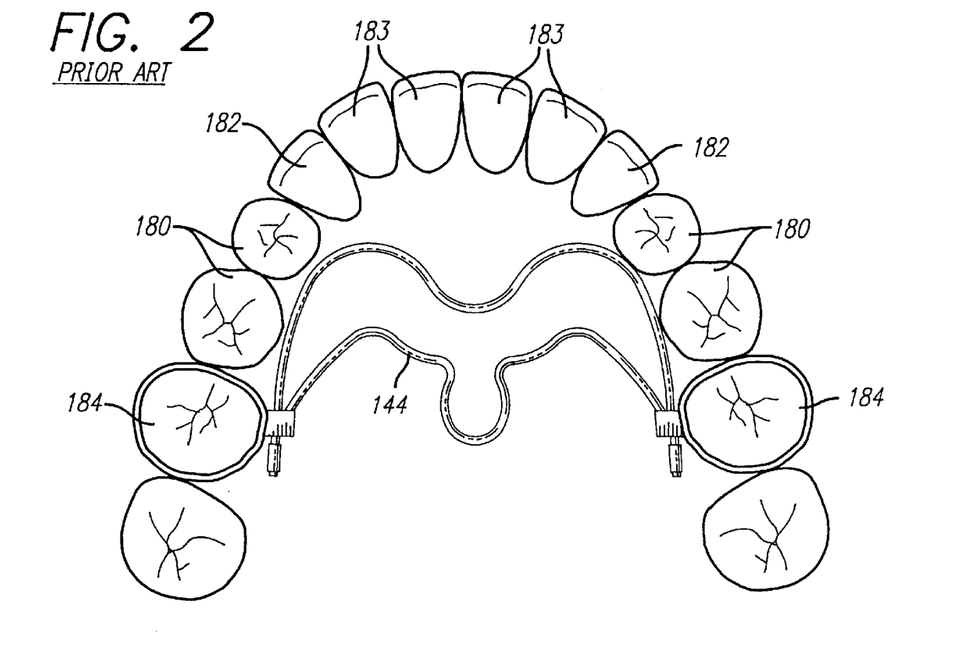
FIG. 2 depicts a prior art palatal arch expander where the archwire is formed from a an alloy of nickel-titanium.

The present invention has fulfilled a need that was lacking in the prior art palatal arch expanders, two of which are depicted in FIGS. 1 and 2. The prior art device shown in FIG. 1 is an example of a palatal arch expander made generally of stainless steel. These types of expanders are difficult to insert into the patient's mouth because they are somewhat inflexible. A further disadvantage is that once installed and adjusted to spread or expand the arch, the forces at the beginning of the treatment are high and the teeth will move quickly, which can cause discomfort to the patient. These types of expanders also must be frequently readjusted requiring many visits to the orthodontist.

The palatal arch expander depicted in FIG. 2, shows an archwire made from a shape memory alloy which will provide low, continual forces to expand the arch, thereby preventing the patient discomfort caused by the stainless steel arch expander. A major disadvantage of the FIG. 2 device is that once installed in the mouth, it cannot be further adjusted, which may be necessary since no two people have the same treatment prescription. More specifically, it is almost always necessary to adjust the position of the molars independently of the expansion of the palatal arch. The prior art devices lack this treatment capability.

Figure 3:
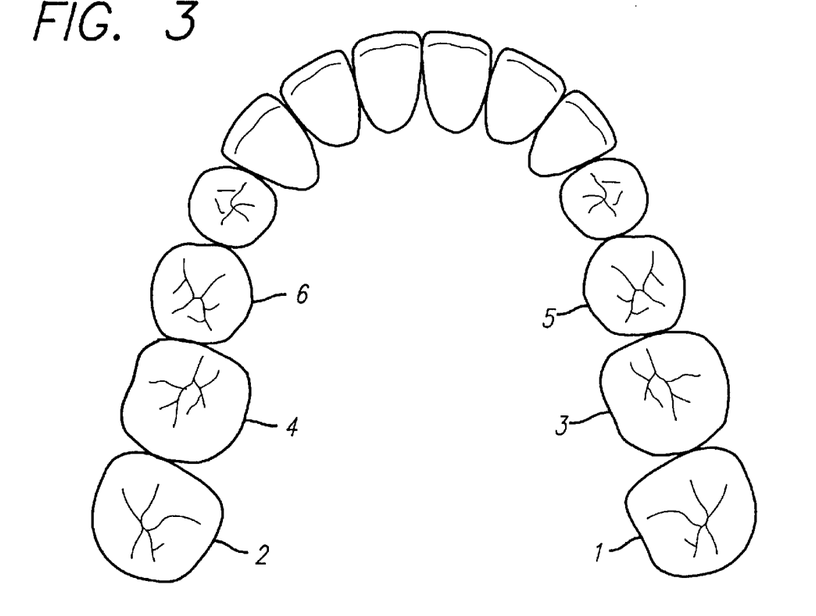
FIG. 3 is a plan view of the palatal arch depicting the teeth generally found in the maxillary arch.

FIG. 3 depicts a typical palatal arch depicting opposed second molars 1, 2, opposed first molars 3, 4, and opposed premolars 5, 6. When crowding occurs between the teeth in the palatal arch, the molars and other teeth must be spread or expanded toward the buccal.

Figure 6:
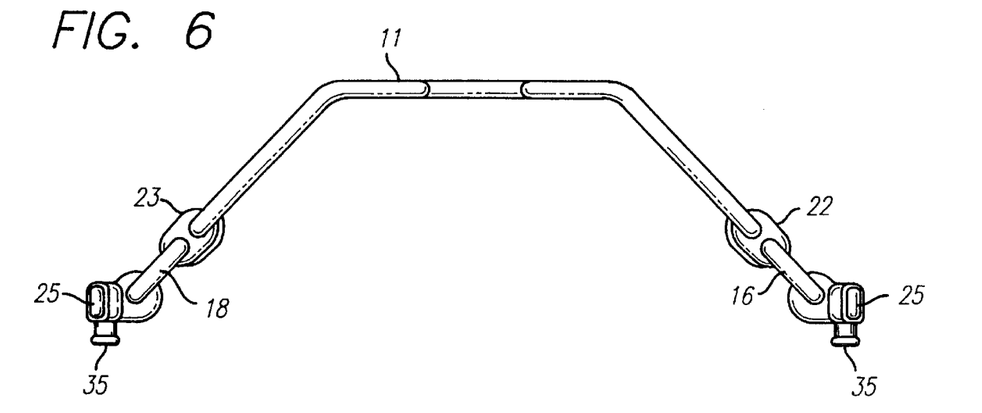
FIG. 6 is an end view of the palatal arch expander assembly of FIG. 4.
Figure 7:
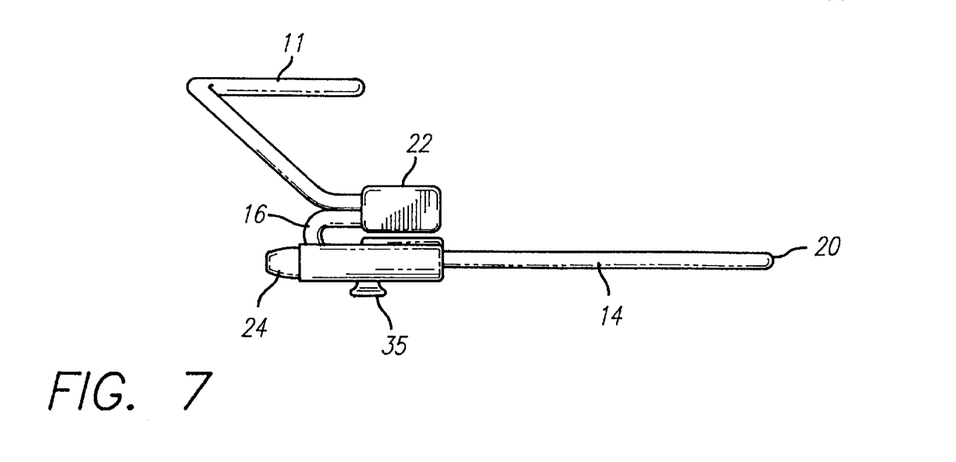
FIG. 7 is a side view of the palatal arch expander assembly of FIG. 4.

The present invention, as depicted in FIGS. 4–7, provides a novel apparatus and method of treatment to expand the palatal arch and allow independent adjustment of the molars. As seen in the drawings, in a preferred embodiment, the palatal arch expander assembly 10 has an archwire 11 that is depicted as having a generally M-shape when viewed as in FIG. 4. Archwire 11 can have other configurations (not shown) and still provide the desired expansion forces. It also is preferred that archwire 11 have a concave shape, as shown in FIG. 6, so that it can approximate the curvature of the palatal arch. It is desirable to position archwire 11 close to the roof of the mouth so that it does not interfere with the tongue, eating, and speech.

Figure 4:
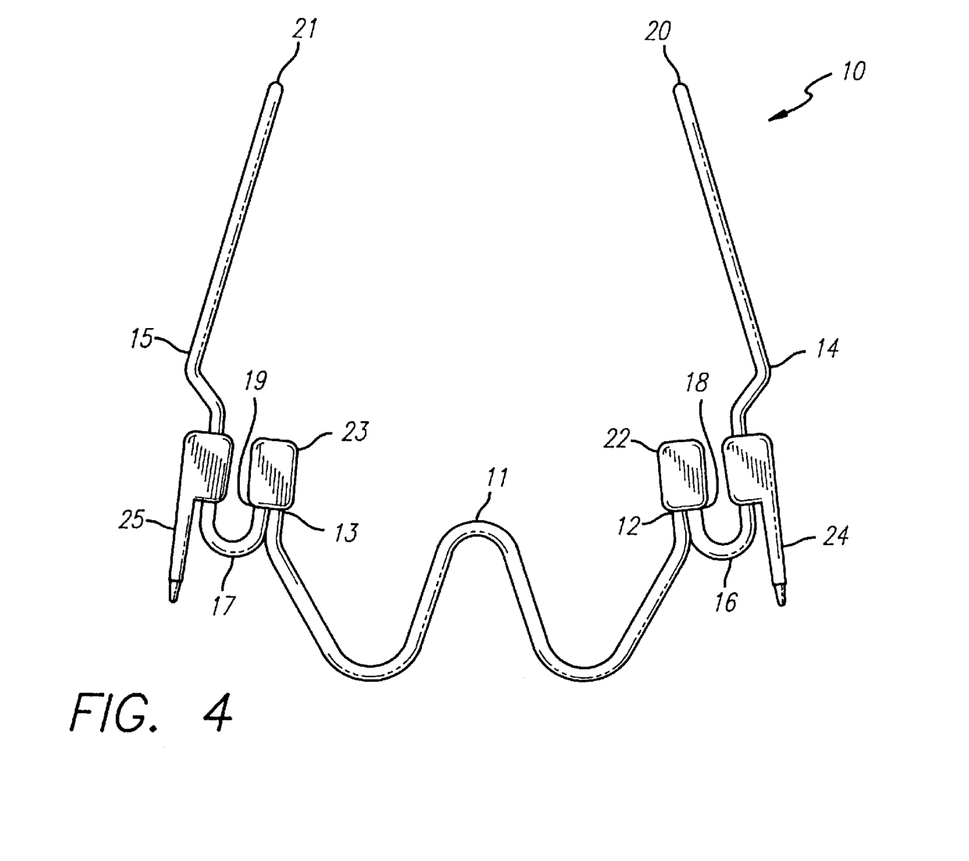
FIG. 4 is a top view of the palatal arch expander assembly of the present invention depicting the relationship between the archwire and adjustment wires.
Figure 5:
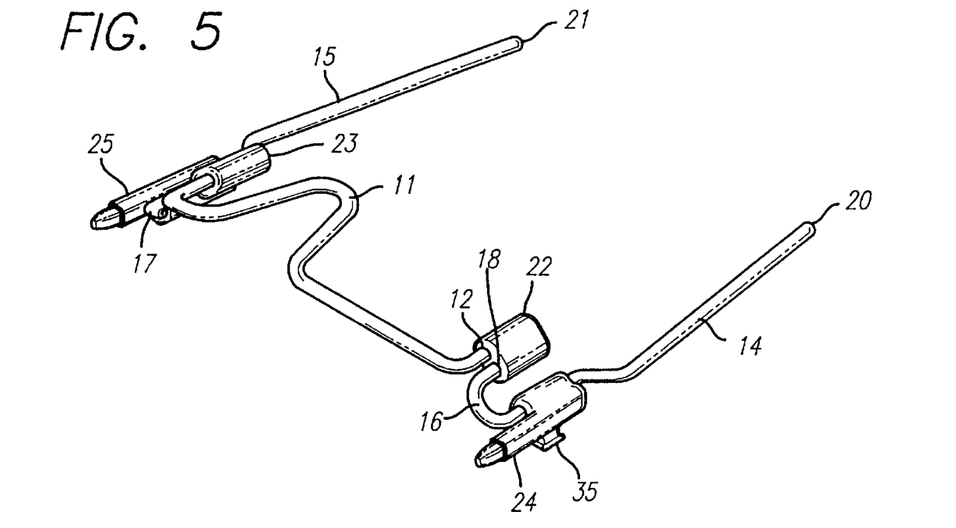
FIG. 5 is a perspective view of the palatal arch expander assembly of FIG. 4.

Archwire 11 has a pair of ends 12, 13, which are used to attach the archwire to the rest of assembly 10. It is preferred that archwire 11 be formed from a shape memory alloy such as nickel-titanium (hereafter NiTi) which can be obtained from many sources, such as Raychem Corporation of Menlo Park, California. Products, such as archwires, made from NiTi have an austenitic state and a martensitic state and a transition temperature therebetween. Shape memory alloys are known in the art and are discussed in Shape-Memory Alloys, Scientific American, Vol. 281, pages 74–82 (November 1979), which is incorporated herein by reference.

Shape memory alloys, like NiTi, undergo a transition between an austenitic state and a martensitic state at certain temperatures. Thus, when in the martensitic state, an archwire made of NiTi will be deformable and easily manipulated. When heated to the transition temperature, however, the archwire attempts to return to its original configuration and it becomes highly flexible, but difficult to bend to different shapes. The temperature at which these transitions occur are affected by the nature of the alloy and the condition of the material. NiTi alloys generally have a transition temperature somewhat below body temperature, which is preferred for the present invention.

The palatal arch expander assembly also includes adjustment wires 14, 15, each of which has a bend 16, 17 for adjusting the molars. Adjustment wires 14, 15 have distal ends 18, 19 and proximal ends 20, 21, respectively. The proximal ends 20, 21 extend anteriorly for a distance, along the lingual surface of the premolars, while distal ends 18, 19 terminate at bends 16, 17. The adjustment wires are attached to the archwire by crimp tubes 22, 23. Distal ends 18, 19 of the adjustment wires and ends 12, 13 of the archwire are received in crimp tubes 22, 23 and the crimp tubes are then partially crushed so that the walls of the tubes firmly hold ends 12, 13 and distal ends 18, 19. The adjustment wires 14, 15 preferably are made of a metal alloy sold under the tradename "Nicoloy" by Elgiloy Ltd., Elgin, Ill. The nicoloy alloy generally has about 39.72% cobalt, 19.92% chromium, 15.24% nickel, 7.27% molybdenum, 2.03% manganese, 0.057% carbon, and the balance made from traces of beryllium, iron, sulfur, phosphorus and silicon. Those having skill in the art will appreciate that the particular nicoloy alloy disclosed here is preferred, however, it is only an example of the many alloy compositions available having similar properties.

The nicoloy alloy permits the adjustment wires 14, 15 to be bent and adjusted either before or after assembly 10 is inserted in the patient's mouth. A nicoloy wire is preferred since it is adjustable and it retains its shape after it is bent so that it will provide corrective forces to the molars as will be described. Adjustment wires 14, 15 also can be made from stainless steel or metal alloys having similar properties.

In keeping with the preferred embodiment, and as is most clearly seen by reference to FIG. 4, adjustment wires 14, 15 extend through stems 24, 25 and are firmly attached thereto either by soldering, welding, brazing, or similar methods of attachment. As will be seen, stems 24, 25 are used to removeably attach palatal arch expander assembly 10 to the molars. Stems 24, 25 can be made from stainless steel or similar materials.

Figure 8:
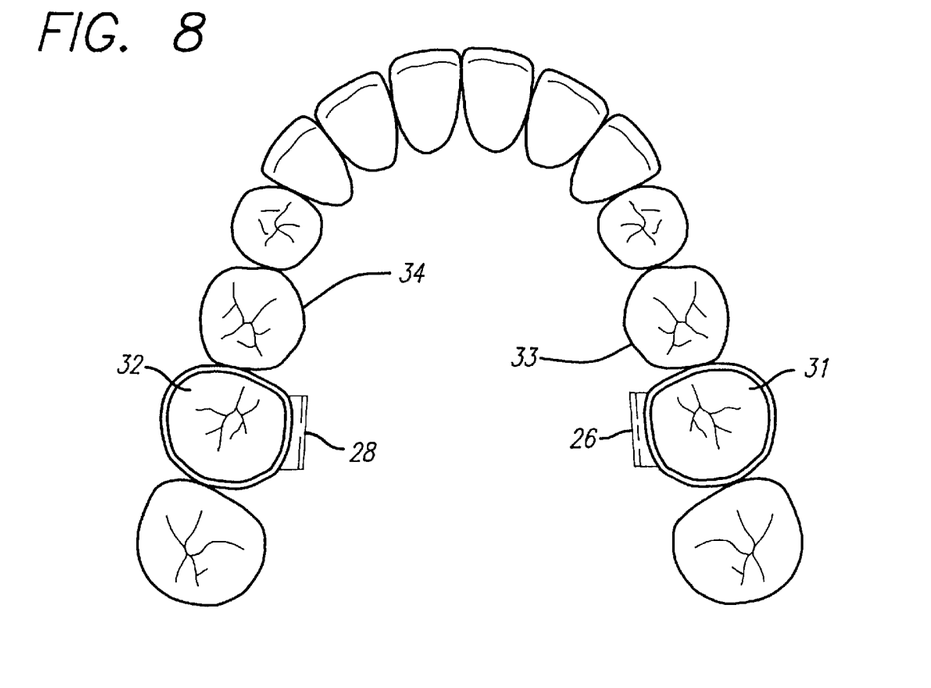
FIG. 8 is a top view of a pair of sheaths mounted on opposed molars before the palatal arch expander assembly of FIG. 4 is inserted into the patient's mouth.
Figure 9:
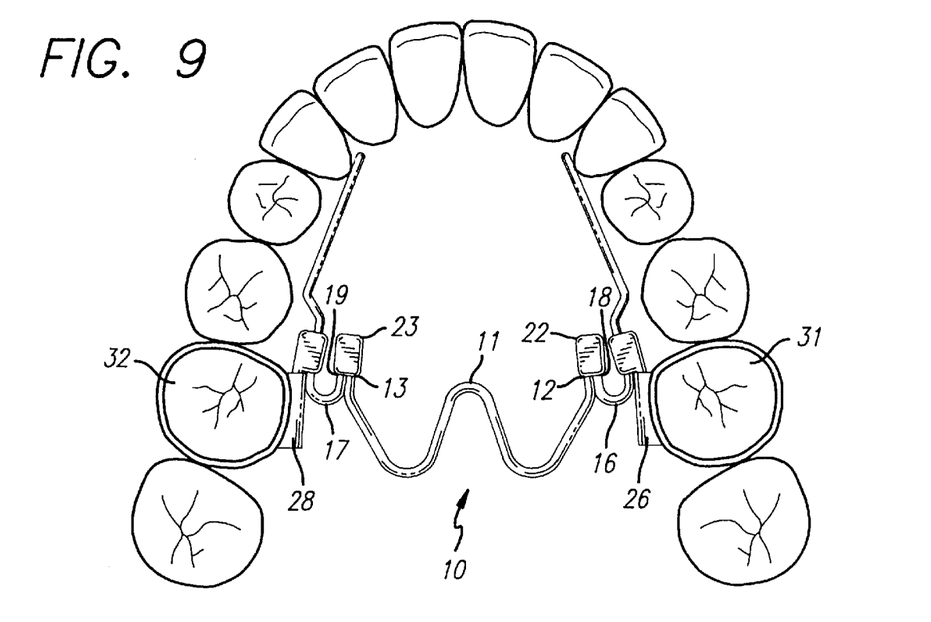
FIG. 9 is a top view of the palatal arch expander assembly of the present invention after it has been inserted into the patient's mouth and properly mounted.

Turning to FIGS. 8 and 9, palatal arch expander assembly 10 is depicted as it is inserted into sheaths 26, 28, which are mounted on the lingual surfaces of opposed molars 31, 32. In keeping with the preferred method of inserting and adjusting assembly 10, prior to insertion the assembly 10 is cooled, and specifically NiTi archwire 11 is cooled with, for example, a refrigerant spray. Once cooled, archwire 11 becomes highly pliable and can be twisted to reduce its size for insertion into the patient's mouth. It also is important to be able manipulate the stems and guide them into sheaths 26, 28. Accordingly, when archwire 11 is sufficiently cooled below its transition temperature to its martensitic state, it can be easily manipulated so that stems 24, 25 can be aligned with and inserted into sheaths 26, 28. A locking detent 35 or similar locking device can be used to ensure that stems 24, 25 do not inadvertently back out of sheaths 26, 28 during the treatment period. The orthodontist also can wire the stems into the sheaths or can use elastics, both of which should prevent stems 24, 25 from inadvertently pulling out of sheaths 26, 28.

After inserting palatal arch expander assembly 10 into the patient's mouth, body heat from the patient will warm archwire 11 so that its temperature will rise above the transition temperature of the NiTi to the austenitic state where it is relatively stiff. The NiTi archwire will then try to return to its original configuration which is to expand outwardly toward the buccal. The archwire will provide low, continuous expansion forces to molars 31, 32, and to the premolars 33, 34 which are in contact with a portion of adjustment wires 14, 15. In this manner, the palatal arch is slowly expanded and the patient should not experience discomfort because the expansion forces are small but continuous.

Figure 10A:
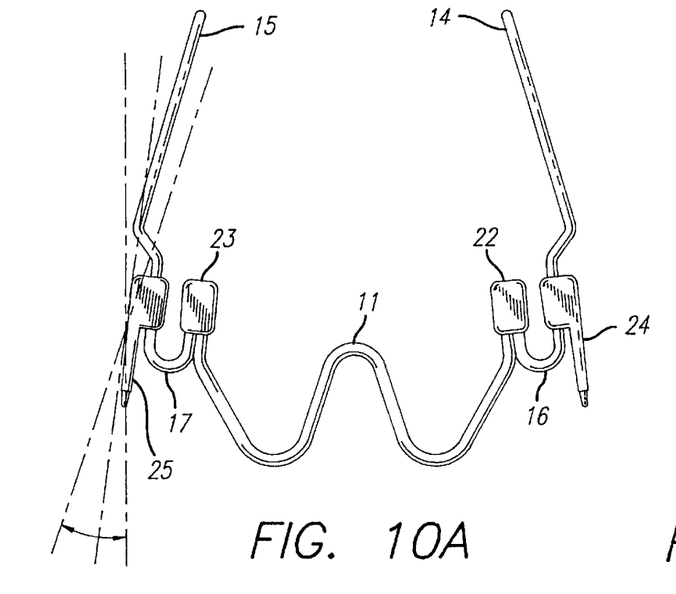
FIG. 10A is a top view of the palatal arch expander assembly depicting the various adjustments available to the bends in the adjustment wires to cause rotation of the molars.
Figure 10B:
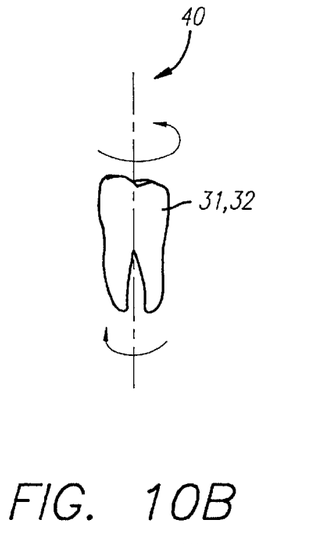
FIG. 10B is a side view of a molar depicting the long axis of the tooth and indicating the rotation imparted to the molar due to the adjustments made to the bends of the adjustment wires as depicted in FIG. 10A.

In keeping with the preferred embodiment, as seen in FIGS. 10A through 12B, means are provided to impart corrective forces to molars 31, 32, independent of the forces imparted by archwire 11. The bends in the adjustment wires can be adjusted and readjusted to impart rotation, torque, and angulation in molars 31, 32. Referring to FIGS. 10A and 10B, rotation is imparted to molars 31, 32 by adjusting bends 16, 17 inwardly or outwardly, i.e., by increasing or decreasing the bend angle. Thus, by way of example, if the bend angle starts out at 180°, and it is desired to rotate the molars about their long axis 40, then bends 16, 17 can be decreased to say 175° which will impart rotation to the molars a specific amount. Conversely, the bend angle can be increased to impart similar but opposite rotation to the molars. Bend angles may range from about 30° to 210° of angulation.

Figure 11A:
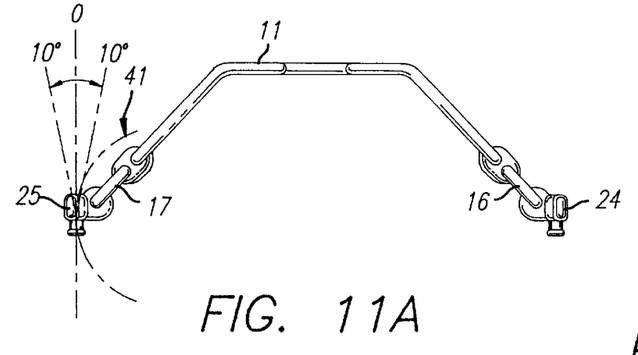
FIG. 11A is an end view of the palatal arch expanded assembly depicting the various adjustments available to the bends in the adjustment wires to cause torque in the molars.
Figure 11B:
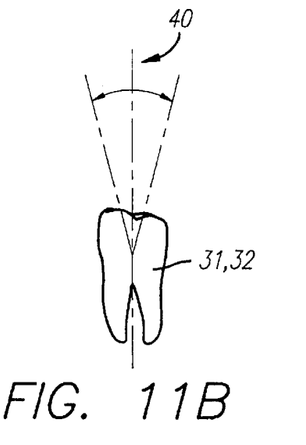
FIG. 11B is a side view of a molar depicting the long axis of the molar and indicating the torque angles imparted to the molar due to the adjustments made to the bends of adjustment wires as depicted in FIG. 11A.

Similarly, and with reference to FIGS. 11A and 11B, the molars can be torqued independently of the forces imparted by archwire 11. Adding torquing forces requires adjusting bends 16, 17 along an arc 41 so an angle of, for example, 100° from the vertical is created. Thus, the crown of the molar essentially is moving toward or away from the buccal a prescribed amount.

Figure 12B:
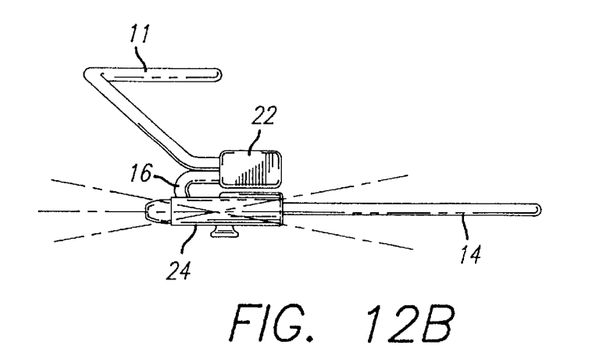
FIG. 12B is a side view of a molar depicting the long axis of the molar and indicating the angulation imparted to the molar due to the adjustments made to the bends of the adjustment wires as depicted in FIG. 12A.

Also in keeping with the preferred embodiment, and as shown in FIGS. 12A and 12B, angulation forces can be imparted to molars 31, 32 by adjusting bends 16, 17. Angulation forces are imparted to the molars by adjusting proximal ends 20, 21 of the adjusting wires up or down as depicted in FIG. 12A. This in turn cause bends 16, 17 to adjust upwardly or downwardly and the same holds true for stems 24, 25. Since stems 24, 25 are attached to the sheaths on the molars, the molars will receive the angulation forces as depicted.

In the preferred embodiment, archwire 11 and adjustment wires 14, 15 have a round cross-section. Other cross-sections, however, are contemplated, such as rectangular or square.

As is known by those having ordinary skill in the art, each patient will require different prescriptions for rotating, torquing, and angulating the molars, thus the amount of correction is left to the orthodontist. It should also be understood that due to the nature of either nicoloy or stainless steel, it may be necessary for the patient to have readjustments made during the treatment period to obtain the optimum rotation, torque and angulation on the molars.

From the foregoing it is apparent that there is described and provided an improved palatal arch expander and method for inserting and adjusting the assembly. While the particular embodiments that have been disclosed are illustrative of an assembly that achieves the advantages of the invention, the disclosed embodiments are illustrative and not intended to limit the invention as it is otherwise defined in the claims.

What is claimed is:

1. A palatal arch expander assembly, comprising:
   an archwire made from a shape memory alloy and configured to substantially span the palatal arch, said archwire having a pair of ends;

a pair of adjustment wires, each said adjustment wire having a distal end and a proximal end, each said distal end having a bend for facilitating the application of correcting forces to the molars such as angulation, rotation or torsion, independent of the forces on each molar and independent of the forces created by the archwire, and each of said proximal ends extending anteriorly for a distance;

a pair of crimp tubes for receiving said ends of said archwire and said distal ends of said adjustment wires;

a pair of stems, each of said stems adapted for receiving said adjustment wires;

whereby the palatal arch expander assembly is mounted in the palatal arch, generally to the lingual surface of opposed molars to expand the palatal arch and to provide correcting forces to the molars such as angulation, rotation or torsion.

2. The palatal arch expander assembly of claim 1, wherein said archwire is made from an alloy of nickel-titanium having an austenitic state and a martensitic state, so that said archwire can be easily manipulated in said martensitic state thereby simplifying installation of said archwire into a patient's mouth.

3. The palatal arch expander assembly of claim 2, wherein said archwire further has a transition temperature which is somewhat below body temperature so that said archwire can be cooled below said transition temperature prior to inserting in the patient's mouth and thereafter warming to about body temperature.

4. The palatal arch expander assembly of claim 1, wherein said adjustment wires are formed from a metal alloy taken from the group of metal alloys consisting of a first metal alloy comprising about 39.72% cobalt, 19.92% chromium, 15.24% nickel, 7.27% molybdenum, 2.03% manganese, 0.057% carbon, and the balance comprising traces of beryllium, iron, sulfur, phosphorus and silicon, and a second metal alloy comprising stainless steel.

5. The palatal arch expander assembly of claim 1, wherein said bends in said adjustment wires are positioned between said crimp tubes and said stems so that said bends will be adjacent the molars when the palatal arch expander assembly is inserted in the patient's mouth.

6. The palatal arch expander assembly of claim 5, wherein said bends in said distal ends of said adjustment wires are from about 30° angulation to about 210° angulation.

7. The palatal arch expander assembly of claim 1, wherein said archwire has a substantially M-shaped configuration.

8. The palatal arch expander assembly of claim 1, wherein said archwire has a substantially concave shape which approximates the concave shape of the palatal arch.

9. The palatal arch expander assembly of claim 1, wherein said archwire has a generally M-shape for reducing expansion forces.

10. A method for applying expansion forces to the palatal arch utilizing an archwire assembly providing low, constant corrective forces provided by an archwire formed of a nickel-titanium alloy, the archwire having a pair of ends for insertion into and attachment to a crimp tube, a pair of adjustment wires each having a distal end and a proximal end, the distal ends of the adjustment wires each having a bend for facilitating the application of correcting forces to the molars such as angulation, rotation or torsion, independent of the forces on each molar and independent of the forces created by the archwire, the distal ends of the adjustment wires being inserted into and attached to the crimp tube, at least a portion of the adjustment wires are attached to a pair of stems, the stems are adapted for insertion into a pair of sheaths mounted on opposed molars, the method comprising:

cooling the archwire to a temperature below its transition temperature so that the archwire is in its martensitic state where it is malleable and can be easily manipulated;

bending the archwire to reduce the overall size prior to insertion into the mouth of the patient;

inserting the archwire assembly into the mouth of the patient and aligning and inserting the stems into the sheaths on the respective molars;

allowing the archwire to warm to a temperature above the transition temperature to the austenitic state;

providing low, constant expansion forces to the palatal arch as the archwire seeks to return to its preformed shape in the austenitic state.

11. The method of expanding the palatal arch of claim 10, wherein the adjustment wires each have a bend positioned between the crimp tube and the stem, the method further comprising adjusting the curvature of the bends in order to apply corrective forces to the molars.

12. The method of expanding the palatal arch of claim 11, wherein said adjusting step on the bends of the adjusting wires provides rotational corrective forces to the molars.

13. The method of expanding the palatal arch of claim 11, wherein said adjusting step on the bends of the adjusting wires provides angulation forces on the molars.

14. The method of expanding the palatal arch of claim 11, wherein said adjusting step on the bends of the adjusting wires provides torsional forces on the molars.

15. The method of expanding the palatal arch of claim 11, wherein said bending step on the adjustment wires can be repeated throughout the treatment period to provide the desired amount of corrective force and movement of the molars.

16. A palatal arch expander assembly, comprising:

an archwire made from a superelastic alloy and configured to substantially span the palatal arch, said archwire having a pair of ends;

a pair of adjustment wires, each said adjustment wire having a distal end and a proximal end, each said distal end having a bend for facilitating the application of correcting forces to the molars such as angulation, rotation or torsion, independent of the forces on each molar and independent of the forces created by the archwire, and each of said proximal ends extending anteriorly for a distance;

a pair of crimp tubes for receiving said ends of said archwire and said distal and said distal ends of said adjustment wires;

a pair of stems, each of said stems adapted for receiving said adjustment wires;

whereby the palatal arch expander assembly is mounted in the palatal arch, generally to the lingual surface of opposed molars to expand the palatal arch and to provide correcting forces to the molars such as angulation, rotation or torsion.

* * * * *

UNITED STATES PATENT AND TRADEMARK OFFICE
CERTIFICATE OF CORRECTION

PATENT NO. : 5,816,800
DATED : Oct. 6, 1998
INVENTOR(S) : Lindsay W. Brehm, Stephen M. Huff, Robert J. Senini It is certified that error appears in the above-identified patent and that said Letters Patent is hereby corrected as shown below:

Figures Sheet 5 of 5, change title of "FIG. 12B", first occurrence, to read --FIG. 12A--.

Signed and Sealed this

Sixteenth Day of February, 1999

Attest:

Attesting Officer

*Acting Commissioner of Patents and Trademarks*